United States Patent
Kim et al.

(10) Patent No.: US 7,118,767 B2
(45) Date of Patent: Oct. 10, 2006

(54) PHARMACEUTICAL COMPOSITION FOR INCREASING THE PRODUCTION OF NITRIC OXIDE AND IFN-γ, AND PROCESS FOR PREPARATION THEREOF

(75) Inventors: Hyung-Min Kim, Jeonlabuk-do (KR); HyungJa You, Kyungki-do (KR); Sang-Bong Seo, Kyungki-Do (KR)

(73) Assignee: Jakwang Co., Ltd. (KR)

( * ) Notice: Subject to any disclaimer, the term of this patent is extended or adjusted under 35 U.S.C. 154(b) by 496 days.

(21) Appl. No.: 10/206,023

(22) Filed: Jul. 26, 2002

(65) Prior Publication Data

US 2003/0031733 A1 Feb. 13, 2003

(30) Foreign Application Priority Data

Jul. 26, 2001 (KR) .................................... 2001-45019

(51) Int. Cl.
*A61K 35/78* (2006.01)

(52) U.S. Cl. ...................................................... 424/725
(58) Field of Classification Search ................. 424/725, 424/195.1; 514/783
See application file for complete search history.

(56) References Cited

U.S. PATENT DOCUMENTS 5,595,756 A * 1/1997 Bally et al. ................. 424/450

* cited by examiner

*Primary Examiner*—Patricia Leith
(74) *Attorney, Agent, or Firm*—Jones Day

(57) ABSTRACT

The present invention relates to a pharmaceutical composition comprising an extract of the mixture of *Coicis Semen, Chicorium intibus, Acanthopanax sessiliflorus* SEEM, *Lonicerae flos, Platycodi radix, Poria, laminariae Thallus, Taraxaci herba, Acori graminei Rhizoma* and *Glycyrrhia uralaensis* FISCH or dry power of the extract for increasing nitric oxide (NO) and INF-γ production and a process for preparation thereof.

11 Claims, 2 Drawing Sheets

Concentration of Liquid preparations of the present invention (mg/ml)

1. Control
2. IFN-γ treated
3. Present Invention (treated)
4. IFN-γ and LPS treated
5. IFN-γ and Present Invention (treated)

PHARMACEUTICAL COMPOSITION FOR INCREASING THE PRODUCTION OF NITRIC OXIDE AND IFN-γ, AND PROCESS FOR PREPARATION THEREOF

This application claims benefit of priority to Korean Application No. 2001-45019 filed on Jul. 26, 2001 in Korea.

BACKGROUND OF THE INVENTION

Field of the Invention

The present invention relates to a pharmaceutical composition for increasing nitric oxide (NO) and IFN-γ production, and a process for preparation thereof. More particularly, the present invention relates to a pharmaceutical composition for increasing nitric oxide (NO) and IFN-1 production and a process for preparing the same, which includes an extract or dry powder of the extract of the mixture of *Coicis Semen, Chicoiium intibus, Acanthopanax sessiliflorus* SEEM, *Lonicerae flos, Platycodi radix, Poria, laminarae Thallus, Taraxaci herba, Acori graminei Rhizoma* and *Glycyrrhiza uralensis* FISCH.

Nitric oxide (NO) is a highly unstable and reactive material, which performs various in vivo actions (Bredt, D. S. and Snyder, S. H.: Nitric oxide, a novel neouronal messenger. *Neuron* 8, 3, 1992; Moncada, S., Palmer, R. M. J. and Higgs, E. A.: Nitric oxide: Physiology, pathophysiology and pharmacology. *Pharmacol. Rev.* 43, 109, 1991; Nathan, C. F. and Hibbs, J. B. Jr.: Role of nitric oxide synthesis in macrophage antimicrobial activity. *Curr, Opinion Immunl.* 3, 65, 1991). Enzymes that synthesize NO are largely grouped into two categories: i.e., a constitutive NO synthase (cNOS) and an inducible NO synthase (iNOS). cNOS is a protein that exists in cells and is activated by certain stimulation while iNOS is a protein that is newly synthesized by stimulation (Nathan, C. F.: Nitric oxide as a secretory product of mammalian cells. *FASEB J.* 6; 3051, 1992; Stuehr, D. J. and Marietta M. A.: Mammalian nitrate biosynthesis: Mouse macrophages produce nitrite and nitrate in response to *Escherichia coli* lipopolysaccharide. *Proc. Natl. Acad. Sci, USA* 82, 7338, 1985). It is already known that a large amount of nitrate ($NO_3$) is produced from experimental animals that were administered with lipopolysaccharide (LPS), an endotoxin (Wagner, D. A., Young V. R. and Tannenbaum, S. R.: Mammalian nitrate biosynthesis: Incorporation of $15H_3$ into nitrate is enhanced by endotoxin treatment. *Proc. Natl. Acad. Sci. USA* 78, 7.764, 1983), and it was verified that macrophages are activated by IFN-γ and LPS thus producing nitrite ($NO_2^-$) and nitrate. The nitrite and nitrate are originated from NO produced in macrophages (Hibbs, J. B., Jr., Taintor, R. R. and Vavrin, Z.: Iron depletion: possible cause of tumor cell cytotoxicity induced by activated macrophages. Biochem. Biophys. Res. Comm-un. 123, 716, 1984). Further, the NO was verified to be an important mediator in antimicrobial activity and anticancer activity of macrophages (Hibbs, J. B., Jr., Taintor, R. R. and Vavrin, Z.: Macrophage cytotoxicity: role for L-arginine deiminase and imino nitrogen oxidation to nitrite. *Science* 235, 473, 1987; Stuehr, D. J. and Nathan, C. F.: Nitric oxide, a macrophage product responsible for cytostasis and respiratory inhibition in tumor target cells. *J. Exp. Med.* 169, 1543, 1989). Therefore, when a certain effective drug promotes NO production of macrophages, the anticancer effect of that drug can be analogized because the amount of NO production from macrophages can serve as a good index for studying anticancer effect.

Meanwhile, immune system can be divided into three different categories: a natural resistance, a non-specific immune system and a specific immune system. The natural resistance (the primary defense line) refers to an immune system where anatomical physiological factors defend against all kinds of invaders including microorganisms regardless of their kinds. The non-specific immune system (the secondary defense line) refers to an immune system which consists of macrophages that remove invaders that came into the body when natural resistance is failed and the specific immune system (the tertiary defense line) is composed of lymphocytes. Of these, the specific immune system is the most advanced immune system which enables to memorize and distinguish self from non-self.

Leukocytes are involved in secondary or tertiary defenses to defend against foreign bodies that have passed through the first defense line. Among the leukocytes, macrophages have many lysosomes that include acidic hydrolase and peroxidase. Also, macrophages adhere strongly to the surface of glass and plastic and actively engulf microorganisms or tumor cells. They have receptors for cytokines such as IFN-γ and produce cytokines such as complement component, interferon, IL-1 and tumor necrosis factor. Functions of macrophages can be increased by various cytokines produced from T-cells.

T-cells, also a kind of leukocytes, take up about 70% of small lymphocytes in blood. T-cells are differentiated from thymus and have T-cell receptors (TCR). Peripheral T-cells are divided into helper T-cells ($T_H$ cells) that are CD4 positive and cytotoxic T-cells ($T_C$ cells) that are CD8 positive. $CD4^+$ TH cells are activated by recognition of antigens that are combined with MHC class II molecules and help B-cells to produce antibodies or help the function of other T-cells. $CD4^+$ TH cells are divided again into $T_H1$ and $T_H2$ according to cytokines they produce. $T_H1$ cells of experimental mice secrete IL-2, IFN-γ, etc., while $T_H2$ cells secrete L-4, IL-5, IL-6, IL-9, IL-10, IL-13, etc. But, in human, the production of IL-2, IL-6, IL-10 and IL-13 is not classified clearly. IL-3, tumor necrosis factor-α (TNF-α), granulocyte-macrophage colony-stimulating factor (GM-CSF), [Met]enkephalin and chemokine (CK) are also secreted without clear classification. $T_H1$ cells are related with cell immune reaction and activate cytotoxicy and inflammatory reaction. Cytokines produced from $T_H2$ cells accelerate antibody formation and especially help IgE production and increase proliferation and function of eosinophils. Therefore, $T_H2$ cytokines are often found in antibody formation and allergic reaction. $T_H1$ and $T_H2$ cytokines function to inhibit each other and it was verified that they can change progress of disease with anti-IL-4 antibody and anti-IFN-γ antibody. And there is a case that injection of IFN-γ to a patient with rheumatoid arthritis brought improvement in symptoms.

As described above, substances that enable to produce a large amount of NO and IFN-γ are expected to have an anticancer effect or an immune enhancing effect.

SUMMARY OF THE INVENTION

The inventors examined closely the producing ability of NO and IFN-γ of a pharmaceutically acceptable composition which is composed of a mixture of natural substances with no side effect and tried to provide a use as an anticancer supplement drug (or an anticancer drug) or an immune enhancing drug with producing ability of NO and IFN-γ of the mixture of natural substances.

Hence, the producing ability of NO was examined by determining the increase of NO production and inducing ability of inducible NO synthase (iNOS) expression caused by various mixtures of natural substances. Inhibitory effect on iNOS production by competitive inhibition agent against NO production was examined. And, producing ability of IFN-γ related with an immune enhancing effect was examined. As a result, extract of mixture of specific natural substances were proved to have excellent ability of increasing NO production and the present invention was finally completed.

Therefore, the object of the present invention is to provide a pharmaceutical composition for increasing NO and IFN-γ production, and the process for preparation thereof, which include extracts or dry powder of the extracts of mixture of *Coicis Semen, Chicorium intibus, Acanthopanax sessiliflorus* SEEM, *Lonicerae Flos, Platycodi Radix, Poria, Laminariae Thallus, Taraxaci Herba, Acori Graminei Rhizoma* and *Glycyrrhiza uralensis* FISCH.

Another object of the present invention is to provide an immune enhancing drug and an anticancer drug that include the above-mentioned composition.

DETAILED DESCRIPTION OF THE INVENTION

Figure 1:
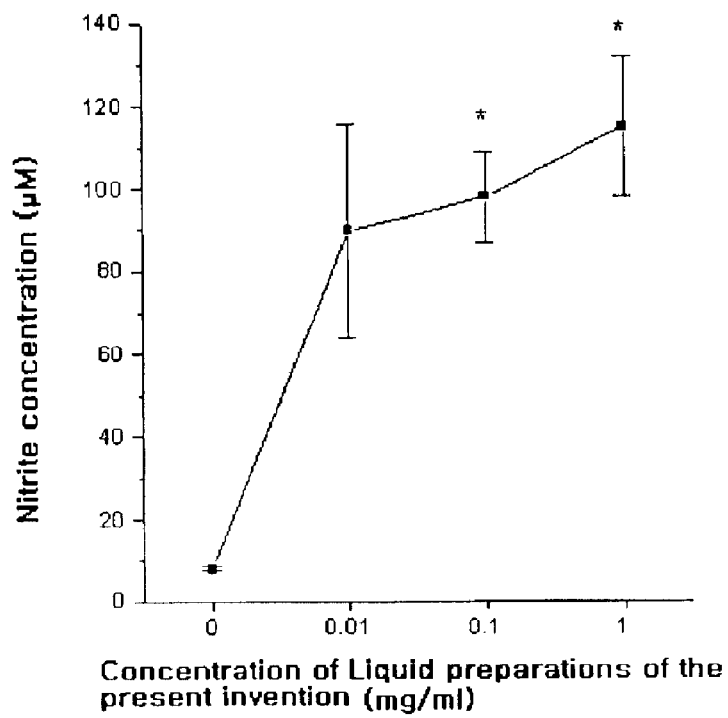
FIG. 1 is a graph indicating the effect of liquid preparations prepared according to Example 1 of the present invention on nitric oxide (NO) production.

The composition for increasing NO and IFN-γ production according to the present invention include, as active ingredients, the extract of a mixture of *Coicis Semen, Chicorium intibus, Acanthopanax sessiliflorus* SEEM, *Lonicerae Flos, Platycodi Radix, Poria, Laminariae Thallus, Taraxaci Herba, Acori Graminei Rhizoma* and *Glycyrrhiza uralensis* FISCH.

For the mixture of *Coicis Semen, Chicorium intibus, Acanthopanax sessiliforus* SEEM, *Lonicerae Flos, Platycodi Radix, Poria, Laminariae Thallus, Taraxaci Herba, Acori Graminei Rhizoma* and *Glycyrrhiza uralensis* FISCH in the composition of the present invention, the desirable weight ratio of *Coicis Semen, Chicorium intibus, Acanthopanax sessiliflorus* SEEM, *Lonicerae Flos, Platycodi Radix, Poria, Laminariae Thallus, Taraxaci Herba, Acori Graminei Rhizoma* and *Glycyrrhiza uralensis* FISCH is 4~16:4~16:2~8:2~8:2~8:2~8:2~8:2~8:1~4:1~4.

The composition of the present invention is especially effective for diseases such as various cancers, decrease of immunological competence, etc.

The present invention is described in more detail as set forth hereunder.

*Coicis Semen*, the active ingredient 1 of the composition of the present invention, is a mature species of rosary and coix that belongs to Graminae. Efficacies such as inducing diuresis, eliminating arthralgia due to dampness, pyocenosis, antidiarrhea are recorded in the books of traditional oriental medicine. Coixenolide, one of the active ingredients, is known to be antioncotic.

*Chicorium intibus*, the active ingredient 2 of the composition of the present invention, has around 75% of moisture and around 25% of solid in its living state. Of the solid, insulin takes up 62.7~71.2%, sucrose 10~13%, cellulose 5~6%, protein 5.5~7%, ash 3.3~3.9% and other components 3.4~11.6%. It is effective in improvement of intestinal colony, intestinal regulation and improvement of lipid metabolism.

*Acanthopanax sessiliflorus* SEEM, the active ingredient 3 of the composition of the present invention, is velamen or bark of *Acanthopanax sessiliflorum*, which belongs to Araliaceae. The above-mentioned ingredient has activity in eliminating wind-dampness (sensation of heaviness of the extremities of the body aggravated by cloudy or rainy weather), restoring Qi (vital energy often referred to as functional activities generally denoting the function of the internal organs and tissues) of liver and kidney, strengthening muscle and bone, so it has been reported that it is administered for pain due to arthralgia syndrome caused by wind and dampness, spasm.

*Lonicerae Flos*, the active ingredient 4 of the composition of the present invention, is the bud of honeysuckle. The ingredient is effective in dissipating heat and detoxifying, dissipating heat from blood, dispersing pathogenic factors that invade body via wind and heat.

*Platycodi Radix*, the active ingredient 5 of the composition of the present invention, is the root of a broad bellflower. The ingredient is effective in ventilating lung and removing phlegm, pyocenosis and regulating Qi flow (flow of 'Qi', vital energy).

*Poria*, the active ingredient 6 of the composition of the present invention, is an irregular type sclerotia which is parasitic on the root of a pine tree. The ingredient is known to be effective in inducing diuresis and excreting dampness, strengthening digestive system, and tranquilization.

*Laminanae Thallus*, the active ingredient 7 of the composition of the present invention, is a thallus of a tangleweed which is a perennial plant of seaweeds. The ingredient is accepted as effective in eliminating phlegm stagnation, relieving thyroid gland disorder.

*Taraxaci herba*, the active ingredient 8 of the composition of the present invention, is whole perennial plant of a dandelion including root. The ingredient is known to be effective in dissipating heat and detoxifying and removing swellings, dispersing tubercle, and especially strong in stagnation dispersing so it is usefully applied to treat diseases such as breast tubercle, tuberculous cervical lymphadenitis.

*Acori Graminei Rhizoma*, the active ingredient 9 of the composition of the present invention, is rhi zoid of a sweet flag, a perennial plant. It is effective for resuscitation, tranquilization, mediating phlegm-dampness (the end product of fluid and humor pathophysiology based on the traditional concept that fluids and humors not only refer to water humours but also include the basic substances that participate in the body's physiological functions, such as electrolytes, neurotransmitters, endocrine hormones, and immunoproteins. Phlegm damp's engenderment from fluids and humors is due to a disturbance in [fluids and humors'] circulation), mediating digestive system, and eliminating impureness.

*Glycyrrhiza uralensis* FISCH, the active ingredient 10 of the composition of the present invention, is root and rhi zoid of *Glycyrrhizae Radix*, a perennial plant. The ingredient is effective in enriching spleen and invigorating Qi, dissipating heat and detoxifying, moistening lung and relieving cough. The ingredient combines many drugs and mitigate severe nature of the drug.

Materials for the composition of the present invention are *Coicis Semen, Chicorium intibus, Acanthopanax sessiliflorus* SEEM, *Lonicerae Flos, Platycodi Radix, Poria, Laminariae Thallus, Taraxaci Herba, Acori Graminei Rhizoma* and *Glycyrrhiza uralensis* FISCH, and the desirable weight ratio of *Coicis Semen, Chicorium intibus, Acanthopanax sessiliflorus* SEEM, *Lonicerae Flos, Platycodi Radix, Poria, Laminariae Thallus, Taraxaci Herba, Acori Graminei Rhizoma* and *Glycyrrhiza uralensis* FISCH when they are mixed is 4~16:4~16:2~8:2~8:2~8:2~8:2~8:2~8:1~4:1~4.

The above-mentioned weight ratio of natural drugs is obtained by repeated experiments. If the amount of one of the ingredients is below the lowest limit, the pharmacological effect of that ingredient diminishes and if it is over the highest limit, pharmacological effect of other ingredients might diminish, thus resulting in diminishment of potentiation and synergy of the composition.

The composition of the present invention can be used as immune enhancing drug and treatment supplement, prevention or treatment drug for cancer. These pharmacological effects are confirmed by Example 1 or 7 mentioned hereinbelow. The composition of the present invention is assumed to control the production of cytokines and chemical mediators from cells in charge of immune system and enhance immunological competence of body locally or wholly.

The composition of the present invention can be prepared into pills, granules and liquids by brewing the above-mentioned natural drugs or by mixing and composing extract which is extracted by solvents such as water, ethanol, methanol and ethyl acetate according to the physicochemical property of the active ingredients, or powder obtained by drying the extract with pharmaceutically acceptable carriers and using a common drug manufacturing method. The composition of the present invention is desirable as liquids considering efficacy, but it can be prepared into pills, granules, tablets or capsules, as occasion demands, and it can be prepared into other formulations when in use.

The composition of the present invention, for example, can be prepared into a decoction by adding 800 mL of water to the mixture of 4~16 g of *Coicis Semen,* 4~16 g of *Chicorium intibus,* 2~8 g of *Acanthopanax sessiliflorus* SEEM, 2~8 g of *Lonicerae Flos,* 2~8 g of *Platycodi Radix,* 2~8 g of *Poria,* 2~8 g of *Laminariae Thallus,* 2~8 g of *Taraxaci Herba,* 1~4 g of *Acori Graminei Rhizoma* and 1~4 g of *Glycyrrhiza uralensis* FISCH and concentrating the mixture to around 150 mL by brewing it for about two hours.

One common dosage of the present composition is 1.5~2.5 mL/kg (body weight) and it is dosed three times a day. For example, for an adult with 60 kg of body weight, one dosage is 90~150 mL, dosed for three times a day. However, the dosage of the composition of the present invention can vary according to weight, age, sex, severity of disease and digestive condition of a patient. For other formulations of the composition, the adequate dosage calculated according to the dosage of the liquids as described above is administered orally.

The present invention is explained in greater detail by using the following examples, however, they should not be construed as limiting the scope of the present invention.

EXAMPLE 1

Preparation of Liquids

Liquids were prepared by mixing 8 g of *Coicis Semen,* 8 g of *Chicorium intibus,* 4 g of *Acanthopanax sessiliflorus* SEEM, 4 g of *Lonicerae Flos,* 4 g of *Platycodi Radix,* 4 g of *Poria,* 4 g of *Laminariae Thallus,* 4 g of *Taraxaci Herba,* 2 g of *Acori Graminei Rhizoma* and 2 g of *Glycyrrhiza uralensis* FISCH with 800 mL of water and concentrating the mixture to around 150 mL by brewing it for about 2 hours.

EXAMPLE 2

Preparation of Other Formulations

Pills, granules, tablets and capsules were prepared from the above-mentioned extracts following the common method in the pharmaceutical field.

EXPERIMENTAL EXAMPLE 1

Confirmation of Toxicity and Side Effect

Liquids prepared according to Example 1 was administered to 30 ICR mice (male, 5 weeks) three times a day for 90 days, the same amount (2.5 mL/kg) that is administered to human (1.5–2.5 mL/kg (body weight)), 5 times the amount (12.5 mL/kg) and 10 times the amount (25 mL/kg), respectively. The mice were observed for 30 days after the administration and on the $30^{th}$ day they were sacrificed and anatomized. As a result, there was no physiological disorder externally nor anatomical disorder in all experiment groups.

EXPERIMENTAL EXAMPLE 2

Analysis of the Amount of NO Production from Macrophages

In this experiment, macrophages were removed from the experimental mice and treated with the liquids of Example 1., and properties related with NO production therefrom were examined. Macrophages were removed from male C57BL/6 mice of 6~7 weeks that were bought in Daehan Biolink (Daejeon, Korea). That is, the mice were intraperitoneal injected with 2.5 mL of 4% thioglycollate, the abdominal cavity was washed with RPMI 1640 after 3~4 days and erythrocytes were removed by RBC lysis. It was floated in dulbeccos minimal essential medium (DMEM) which include 10% fetal bovine serum (FBS) and cultivated in $CO_2$ incubator after being divided into Swell by $2.5 \times 10^5$ cells/well. After about 3 hours, culture media was changed, and cells that were not adhered to the surface of the culture container were removed and only adhered cells were used for experiment.

The amount of NO production from macrophages was measured by Griess reaction by quantitizing nitrite ($NO_2^-$), oxides of NO, accumulated on the broth. That is, 100 μL of Griess reagents in which 0.1% naphthylethylene diaminedihydrochloride and 1% sulfanilamide is mixed at the same amount and 100 μL of culture media was mixed, and after 10 minutes, absorbance was measured at 540 nm by ELISA reader. Standard curve using sodium nitrite as standard substance was drawn and the concentration of NO was determined from the absorbance.

FIG. 1 shows the result. As shown in FIG. 1, when the macrophages were treated with liquids of Example 1, the amount of NO production increased by up to 14 times compared to the control group.

EXPERIMENTAL EXAMPLE 3

Determination of Inducing Ability of Inducible NO Synthase (iNOS) Expression

In this experiment, the ability of the composition prepared according to the present invention in inducing the expression of iNOS, an enzyme that synthesizes NO in macrophages, was examined. Experiments were carried out in a control group with no treatment to the macrophages (group 1), a group with no treatment with liquids of Example 1 after treatment with IFN-γ (10U/mL) (group 2), a group with treatment with liquids (1 mg/mL) of Example 1 without treatment of IFN-γ (group 3), a group with treatment with lipopolysaccharides (10 μg/mL) after treatment with IFN-γ (group 4) and a group with treatment with liquids of Example 1 after treatment with IFN-γ (group 5). Lipopolysaccharide (LPS) of *Escherichia coli* was used as lipopolysaccharides. Lipopolysaccharides compose the cell walls and perform the role of stimulant on cells by playing the same role as antigens, therefore, group 4, which is treated with lipopolysaccharides, is regarded as a positive comparative group.

Figure 2:
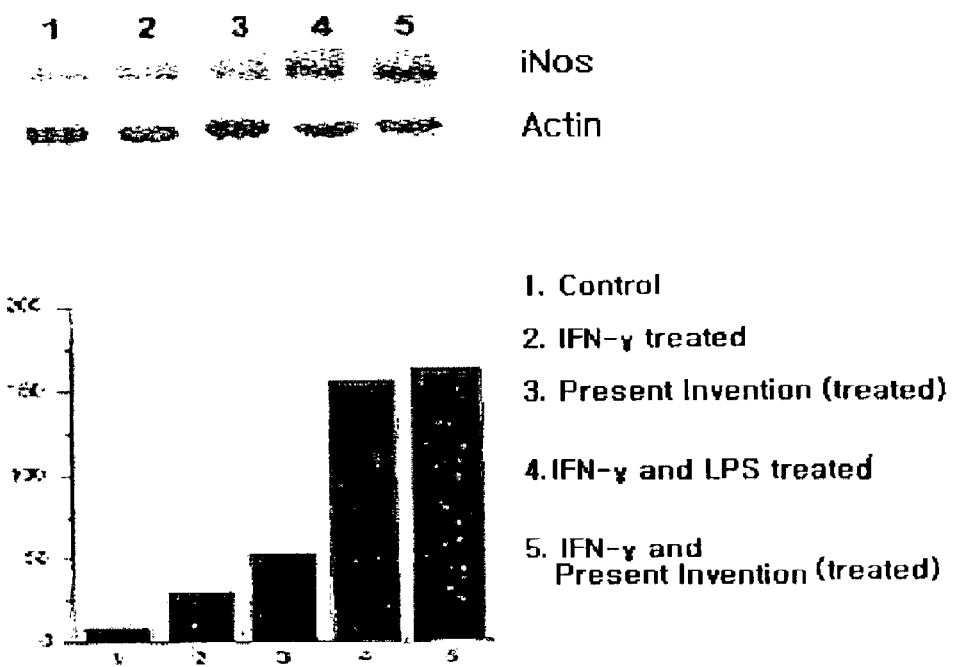
FIG. 2 is a graph indicating inducing ability of inducible NO synthase (iNOS) expression by liquid preparations prepared according to Example 1 of the present invention.

The results are shown in FIG. 2. Here, intensity was measured by using densitometer. As described in FIG. 2, treatment with IFN-γ and the composition of the present invention resulted in no less amount of iNCS expression than treatment with IFN-γ and lipopolysaccharides (positive comparative group; group 4). This means that the composition of the present invention is as effective as the positive comparative group. And, there was a significant increase in intensity when treated with IFN-γ and the composition of the present invention (group 5) as compared to treatment with IFN-γ only (group 2). In conclusion, the inducing ability of iNOS expression largely increased when treated with both IFN-γ and liquids of Example 1.

EXPERIMENTAL EXAMPLE 4

Determination of Inhibitory Effect of iNOS Production by $N^G$MMA ($N^G$-monomethyl-L-arginine)

Figure 3:
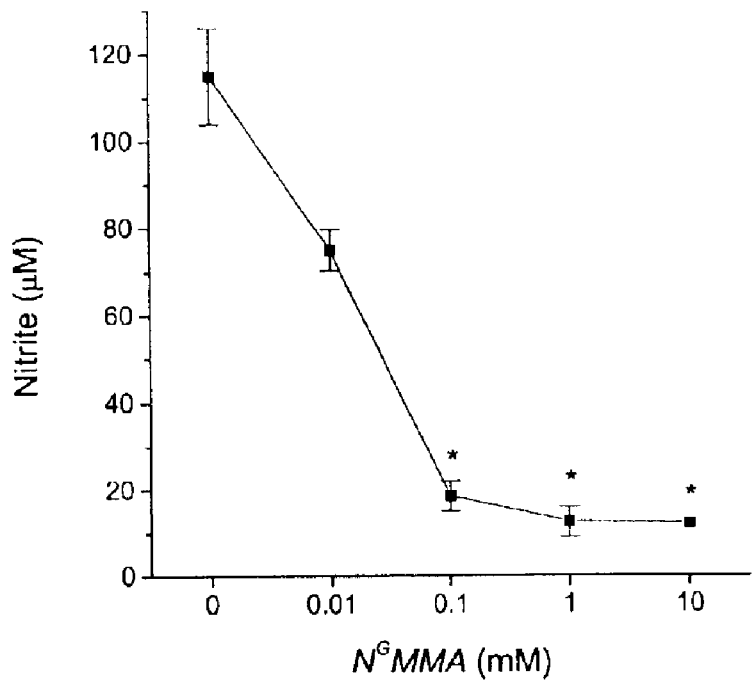
FIG. 3 is a graph indicating inhibiting effect of $N^G$-monomethyl-L-arginine ($N^G$MMA) against iNOS production by liquid preparations prepared according to Example 1 of the present invention.
Figure 4:
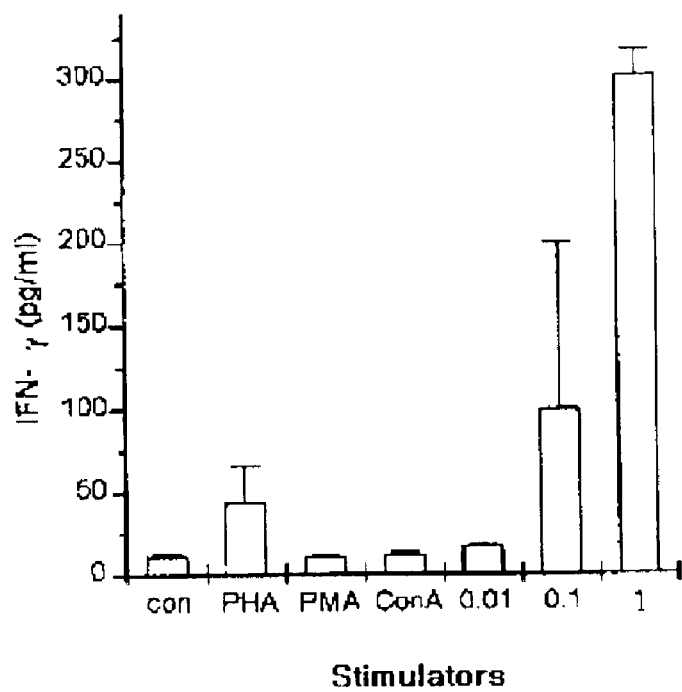
FIG. 4 is a graph indicating effect of liquid preparations prepared according to Example 1 of the present invention on IFN-γ production.

To investigate if iNOS production from macrophages by the composition of the present invention is included in L-arginine-dependent process, the macrophages were treated liquids (1 mg/mL) of Example 1 in the presence of IFN-γ and NGMMA, the competitive inhibitor of NO production, and the amount of NO production was measured by the same method as Experiment 2. The result is shown in FIG. 3. As described in FIG. 3, the amount of NO production had a tendency to decrease as the amount of $N^G$MMA increases.

Therefore, NO production of the composition of the present invention is assumed to be included in L-arginine-dependent process.

EXPERIMENTAL EXAMPLE 5

Determination of Inhibiting Effect on iNOs Production by NF-kB Inhibitor

The purpose of this experiment was to find out the process of NO production of the composition of the present invention. NF-kB, a transcription factor, is known to play an important role as a mediator of protein expression related with immune reaction and inflammatory reactions and iNOS expression depends on activation of NF-kB.

Hereupon, macrophages were treated with recombinant IFN-γ (rIFN-γ) and liquids (1 mg/mL) of Example 1 followed by treatment with pyrrolidine dithiocarbamnate (PDTC) and $N^α$-Tosyl-phenylalanyl chloromethyl ketone (TPCK), which are NF-kB inhitors, respectively and the change of concentration of $NO_2^-$ was observed together with control group. The results are shown in the hereinbelow Table 1 [Inhibitory effect on iNOS production by NF-kB inhibitor].

TABLE 1

| Added materials and the amount | | | | |
|---|---|---|---|---|
| rIFN-γ (10 U/mL) | Liquids of Example 1 (1 mg/mL) | PDTC (100 μM) | TPCK (40 μM) | Concentration of $NO_2^-$ |
| − | − | − | − | <5 |
| + | − | − | − | 32 ± 3.2 |
| + | + | − | − | 115 ± 11 |
| + | + | + | − | 10.5 ± 2.8 |
| + | + | − | + | 45.7 ± 3.0 |

As shown in Table 1, NF-kB inhibitor, PDTC or TPCK, significantly inhibited the producing effect of NO of the composition of the present invention. Therefore, NO production of the composition of the present invention is confirmed to be caused by activation of NF-kB.

EXPERIMENTAL EXAMPLE 6

Determination of Ability to Produce Tumor Necrosis Factor-α

Since taxol, an anticancer drug of natural origin, has producing ability of tumor necrosis factor-α (TNF-α) from abdominal macrophages of a mouse, anticancer efficacy was confirmed by determining the ability of producing TNF-α from the composition of the present invention in this experiment. Macrophages ($3 \times 10^5$ cells/well) were cultivated in $CO_2$ incubator (37° C., 5%) with 10 U/mL of rIFN-γ. After 6 hours, freeze-dried powder of liquids of Example 1 was diluted in phosphate buffered saline (PBS) and treated in each concentration (0.01, 0.1 and 1 mg/mL). LPS was used as a stimulant of macrophages. It was cultivated for 24 more hours after treatment with liquids of Example 1, and the amount of TNF-α production was measured by ELISA. The results are shown in the following Table 2 [Producing ability of TNF-α]

TABLE 2

| Added materials and the amount | | | |
|---|---|---|---|
| rIFN-γ (10 U/mL) | Liquids of Example 1 (mg/mL) | LPS (10 μg/mL) | TNF-α (ng/mL) |
| − | − | − | 25 ± 0.03 |
| − | +(1) | − | 0.78 ± 0.03 |
| + | − | + | 22.90 ± 2.7 |
| − | +(0.01) | − | 1.00 ± 0.02 |
| + | +(0.1) | − | 1.34 ± 0.09 |
| + | +(1) | + | 11.69 ± 0.11 |

As described in Table 2, treatment with rIFN-γ and LPS at the same time, significantly increased the amount of TNF-α production (positive comparative group). In case of treatment with liquids of Example 1 instead of LPS, the higher the concentration, the larger the amount of TNF-α production resulting in more than ½ amount of the positive comparative group. This proves that the composition of the present invention promotes TNF-α production in high concentration by collaboration with IFN-γ. As a result, the composition of the present invention is confirmed to be in concentration-dependent relationship with TNF-α production.

EXPERIMENTAL EXAMPLE 7

Determination of Increasing Effect on IFN-γ Production

As described above, IFN-γ is a cytokine secreted from $T_H1$ cells playing an important role in immune function and the increase thereof can be understood as an index of increase of immunological competence. For this experiment, malt-4, one of $T_H1$ cell lines, was bought from KCLB (Korean Cell Line Bank) and cultivated. Cultivated cells were seeded in a 4-well plate by $2\times10^5$ cells/well and stabilized for 30 minutes. They were treated with liquids of Example 1 or other stimulants such as PHA (Phytohemagglutinin), PMA (Phorbol 12-myristate 13-acetate) and ConA (concanavalin A), respectively and IFN-γ production was determined by ELISA after 24 hours.

The results are shown in Table 4. As described in Table 4, the composition of the present invention has a tendency to significantly increase the amount of IFN-γ production depending on concentration.

The composition of the present invention was proved to be effective for increase of NO and IFN-γ production. Producing ability of NO and IFN-γ is related with anticancer and immune enhancing effect, directly and indirectly. Therefore, in modern industrial society where various carcinogenic substances are open in the air, the composition of the present invention can be very useful as prevention and treatment or treatment supplement drug for cancers of various kinds. It can also be useful as preventive or an immune enhancing drug against decrease of immunological competence that is easily caused by abuse of environmental pollution materials and many toxic food additives. Particularly, the composition of the present invention is expected to have excellent immune enhancing effect for examinees and company employees who are under various kinds of stress and lack in adequate amount of exercise.

What is claimed is:

1. A pharmaceutical composition comprising an extract of a mixture of 4–16 parts of *Coicis Semen*, 4–16 parts of *Chicorium intibus*, 2–8 parts of *Acanthopanax sessiliflorus* SEEM, 2–8 parts of *Lonicerae Flos*, 2–8 parts of *Platycodi Radix*, 2–8 parts of *Poria*, 2–8 parts of *Laminariae Thallus*, 2–8 parts of *Taraxaci Herba*, 14 parts of *Acori Graminei Rhizoma* and 1–4 parts of *Glycyrrhiza uralensis* FISCH.

2. The pharmaceutical composition according to claim 1, wherein said pharmaceutical composition further comprises a pharmaceutically acceptable carrier.

3. The pharmaceutical composition according to claim 1, wherein said pharmaceutical composition is suitable for oral administration to a patient.

4. The pharmaceutical composition according to claim 1, wherein said pharmaceutical composition is capable of increasing interferon-γ (IFN-γ) production in a mammal.

5. The pharmaceutical composition according to claim 1, wherein said pharmaceutical composition is capable of increasing nitric oxide (NO) production in a mammal.

6. The pharmaceutical composition of claim 1 wherein said extract is in a form of dry powder.

7. A dosage form which comprises the extract of claim 1.

8. The dosage form according to claim 7, wherein said dosage form further comprises a pharmaceutically acceptable carrier.

9. The dosage form according to claim 7, wherein said dosage form is suitable for oral administration to a patient.

10. The dosage form according to claim 9, wherein said dosage form is a tablet, capsule, liquid, or a granule.

11. The dosage form according to claim 10, wherein the amount of said liquid is 90–150 ml.

* * * * *